United States Patent
Middleton

(10) Patent No.: US 7,090,778 B2
(45) Date of Patent: *Aug. 15, 2006

(54) DEVICE AND METHOD FOR PREVENTING GROWTH OF BACTERIA OR REMOVING BACTERIA IN DUCT OF DENTAL UNIT

(75) Inventor: David L. Middleton, Hyogo (JP)

(73) Assignee: Bio-Signal Corporation Ltd., Channel Island (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/477,824

(22) PCT Filed: May 14, 2001

(86) PCT No.: PCT/JP01/03978

§ 371 (c)(1),
(2), (4) Date: Apr. 1, 2004

(87) PCT Pub. No.: WO02/091943

PCT Pub. Date: Nov. 21, 2002

(65) Prior Publication Data

US 2004/0154992 A1 Aug. 12, 2004

(51) Int. Cl.
C02F 1/36 (2006.01)
B03B 3/08 (2006.01)
A61L 2/02 (2006.01)
B08B 9/027 (2006.01)
B08B 7/02 (2006.01)

(52) U.S. Cl. .................... 210/748; 210/764; 422/20; 134/166 R; 134/22.1

(58) Field of Classification Search .......... 210/748, 210/764; 134/22.11, 166 C, 22.1, 166 R; 422/22, 20

See application file for complete search history.

(56) References Cited

U.S. PATENT DOCUMENTS

| | | | | | |
|---|---|---|---|---|---|
| 4,942,868 A | * | 7/1990 | Vago | | 601/2 |
| 5,048,520 A | * | 9/1991 | Vago | | 601/2 |
| 5,178,134 A | * | 1/1993 | Vago | | 601/2 |
| 5,382,162 A | * | 1/1995 | Sharp | | 433/116 |
| 5,645,697 A | * | 7/1997 | Middleton et al. | | 204/155 |
| 5,665,141 A | * | 9/1997 | Vago | | 95/30 |
| 6,086,369 A | * | 7/2000 | Sharp et al. | | 433/118 |
| 6,106,771 A | * | 8/2000 | Fitton | | 422/14 |

(Continued)

FOREIGN PATENT DOCUMENTS

DE 199 08 997 C1 10/2000

(Continued)

OTHER PUBLICATIONS

Translation of The International Preliminary Examination Report from PCT International Bureau dated Dec. 23, 2003 for International application No. PCT/JP01/03978.

(Continued)

*Primary Examiner*—Fred G. Prince
(74) *Attorney, Agent, or Firm*—Marshall, Gerstein & Borun LLP

(57) ABSTRACT

A device (1) for preventing the growth of the bacteria or removing the bacteria bred on the inner wall surfaces of the ducts (8, 9, 10) of a dental unit, comprising a transponder (3) having a control unit (2) generating electric signals including audible frequency components, a coil (3a), and a case (3b) for storing the coil (3a) and mounting means (5) for mounting the transponder (3) on the outer wall surface of the duct (8), whereby an audible frequency electric signal allowed to transmit through the ducts (8, 9, 10) is generated by applying the electric signals to the coil (3a).

20 Claims, 4 Drawing Sheets

U.S. PATENT DOCUMENTS

| | | | |
|---|---|---|---|
| 6,482,370 B1 * | 11/2002 | Holsclaw et al. | 422/186.12 |
| 6,503,449 B1 * | 1/2003 | Smith | 422/20 |
| 6,510,857 B1 * | 1/2003 | Middleton | 134/22.1 |
| 6,555,055 B1 * | 4/2003 | Cisar et al. | 422/28 |
| 6,624,539 B1 * | 9/2003 | Hansen et al. | 310/26 |

FOREIGN PATENT DOCUMENTS

| | | |
|---|---|---|
| EP | 1 046 611 A1 | 10/2000 |
| JP | 2000-042008 A1 | 2/2000 |
| JP | 2001-149391 | 6/2001 |
| WO | WO-98 57546 | 12/1998 |
| WO | WO9924352 | 5/1999 |

OTHER PUBLICATIONS

Examination Report (in Japanese) date May 14, 2001.

The International Search Report for International Application No. PCT/JP01/03978 dated Jul. 31, 2001 by the JPO.

Supplementary European Search Report received in International (EP) Application 01 93 0099, by the European Patent Office, dated Mar. 2, 2006.

* cited by examiner (a)

(b)

(c)

DEVICE AND METHOD FOR PREVENTING GROWTH OF BACTERIA OR REMOVING BACTERIA IN DUCT OF DENTAL UNIT

TECHNICAL FIELD

The present invention in this application relates to an apparatus and method for preventing growth of microbia propagating themselves on an internal wall of a waterline of a dental unit or for removing the microbia.

BACKGROUND ART

In a dental clinic, a dental unit in which various treatment instruments and treatment goods are arranged around a dental chair is installed. The dental unit includes, as treatment instruments using water, a handpiece for grinding a tooth (tooth grinding tool), a scaler for removing tartar (tartar removing tool), a syringe for cleaning a mouth (mouth cleaning tool), and the like to which service water is supplied.

In the case where the dental unit is installed in a room of a building, a connection box for relay in the dental unit, a tap of a washstand, and the like are connected to a waterline which is branched from a main pipe for receiving supply of a service water chlorinated in accordance with a predetermined environmental sanitation standard and which is led into the room.

To the connection box, an airline from a compressor for discharging compressed air is usually also connected. The airline and the waterline are connected to a control center via the unit body.

To the control center, a plurality of tubes whose tips are provided with the handpiece, the syringe, and a vacuum cleaner for discharging water are connected, and a lead wire from a foot switch and the like is also connected.

When any of the switches of the instruments is turned on at the time of treatment, the control center transmits high-pressure water to the handpiece side via the tube and the high-pressure water rotates a turbine cutter attached to the head of the handpiece, thereby enabling grinding of a tooth. The control center also supplies low-pressure water to the syringe via the tube so that the water is injected into the mouth. In such a manner, tooth treatment can be performed by using service water.

In the waterline connected to the dental unit, differently from a general water pipe, microbia and bacteria easily propagate themselves. It is feared that the water used for treatment of teeth is bad for the health of the patient.

Specifically, each of the waterlines to the handpiece, syringe, scaler, a water supplier for rinsing out the mouth, and the like from which water is supplied directly to the mouth of a patient is branched in some midpoint and its diameter decreases toward the end side. On the side of the treatment instruments connected to the waterlines, water is not always used. Therefore, retention time of the water in the waterlines tends to be long.

In dental clinics, the room temperature is maintained almost constant in all seasons. Consequently, even when the temperature of service water sent to the main pipe side is low, the water temperature in the waterlines rises by being influenced by the higher room temperature of the dental clinics. The environment of the internal wall face of the waterline is suitable for culturing microbia.

Consequently, even when the number of colonies of microbia and bacteria included in one milliliter of chlorinated service water is a few on the main pipe side as the source of water, it sharply increases on the waterline side of the dental unit in which the temperature is about room temperature. There is a case that the number of colonies increased to several hundreds of thousands on the end side of each of the waterlines attached to the various treatment instruments.

As described above, when microbia and bacteria increased in the waterline enter the body through the mouth of a patient at the time of treatment, they may cause various diseases and, what is more, a problem of hospital infection arises. Consequently, it has been expected that effective means for sterilizing water in a waterline used in a dental clinic, a dental department in a hospital, and the like is developed.

An object of the invention is to provide an apparatus and method for preventing growth of microbia and bacteria on an internal wall of a waterline of a dental unit or for removing them, thereby enabling a problem that the patient is infected in a clinic or hospital to be avoided.

DISCLOSURE OF THE INVENTION

To solve the problems, according to the present invention, there is provided an apparatus for preventing growth of microbia propagating themselves on an internal wall of a waterline of a dental unit or for removing the microbia, comprising:

electric signal generating means for generating an electric signal including an audio frequency component; a transponder including a coil and a case for housing the coil; and means for attaching the transponder to an external wall of the waterline, wherein the electric signal is applied to the coil so that an audio electronic signal to be sent through the waterline can be generated.

And according to the invention, there is provided a method for preventing growth of microbia propagating themselves on an internal wall of a waterline of a dental unit or for removing the microbia, comprising the steps of:

generating an electric signal including an audio frequency component; attaching a transponder including a coil and a case for housing the coil to an external wall of the waterline; and applying the electric signal to the coil, thereby generating an audio electronic signal to be sent through the waterline.

According to the apparatus and method, growth of microbia can be prevented by the audio electronic signal. The audio electronic signal is sent through a waterline so that an effect of prevention of the growth of the microbia can be obtained within a wide range of the waterline.

In particular, if the electric signal frequency-modulates around a predetermined frequency and the frequency modulation causes the audio electronic signal to include a harmonics component, the effect becomes more conspicuous.

Preferably, the predetermined frequency is between 1500 Hz and 2500 Hz.

When a face of the transponder which comes in contact with the waterline has a concave shape whose section is circular, an attaching state of a transponder to a waterline can be stabilized.

It is preferable that the transponder is attached near an end of the waterline.

BEST MODE FOR CARRYING OUT THE INVENTION

Representative microbia growing in a waterline are *psuedomonas, klebsiella, legionella, mycobacterium, mesophilic, heterotrophic,* and *moraxella.*

In this specification, microbia include bacteria and yeast. The present invention is mainly effective at preventing microbia from growing in a waterline or removing the microbia in the waterline.

An embodiment of the present invention will be described below with reference to the drawings.

Figure 1:
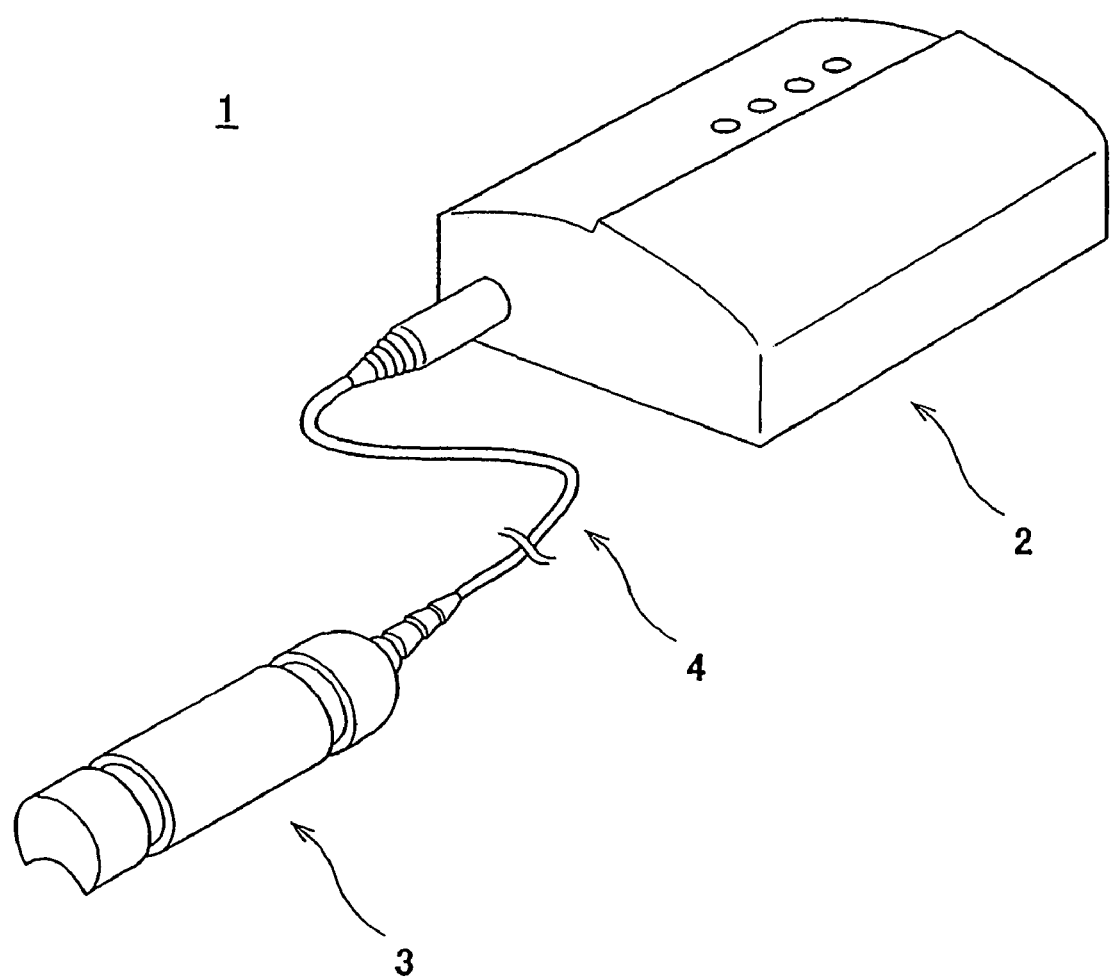
FIG. 1 is a view showing an external appearance of an apparatus according to an embodiment of the present invention.
Figure 2:
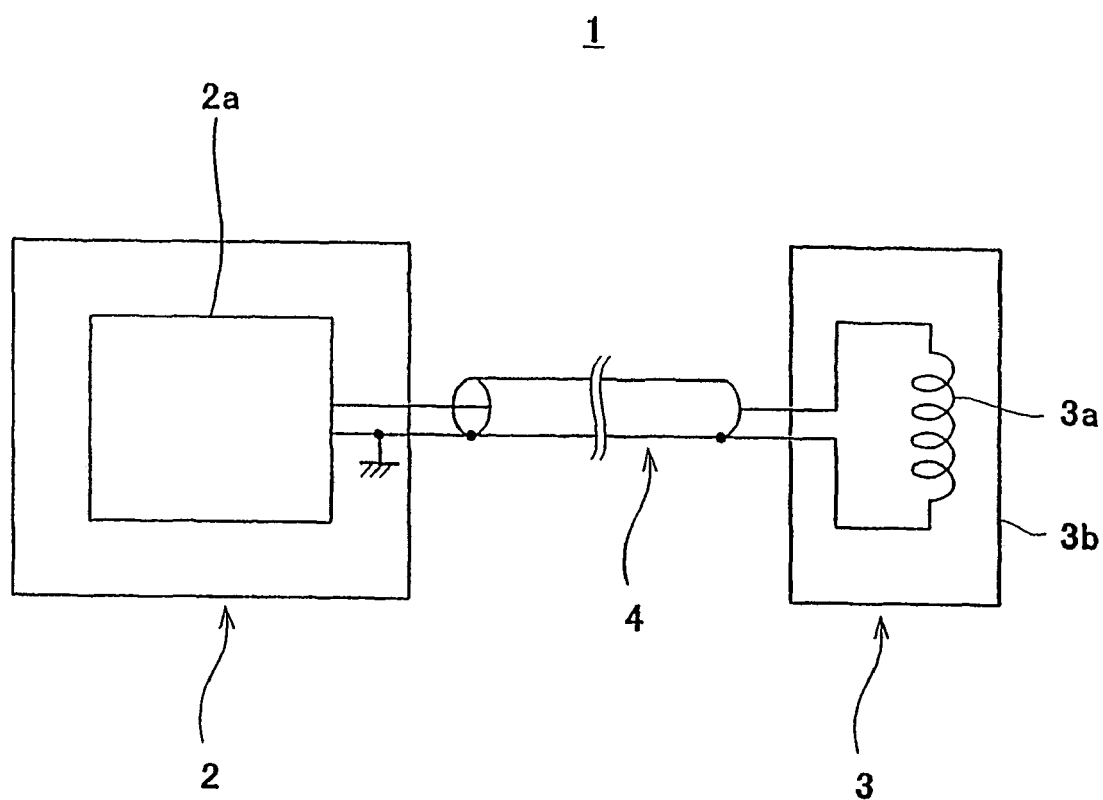
FIG. 2 is a schematic block diagram showing the apparatus according to the embodiment of the present invention.

FIG. 1 is a view showing an external appearance of an apparatus according to an embodiment of the present invention, and FIG. 2 is a schematic block diagram showing the apparatus.

In FIG. 1, the reference numeral 1 denotes the apparatus according to the embodiment of the present invention, the reference numeral 2 denotes a control unit, the reference numeral 3 denotes a transponder, and the reference numeral 4 denotes a coaxial cable.

The control unit 2 acting as electric signal generating means has a voltage capacitor oscillator 2a provided therein. The voltage capacitor oscillator 2a is a main part for generating an electric signal, and serves to generate an electric signal which fluctuates in a range of 2000 Hz±40 Hz.

In other words, the electric signal frequency-modulates in a range of 1960 Hz to 2040 Hz. A center frequency is not always 2000 Hz but any audio frequency can be used. In particular, it is preferable that a specific frequency between 1500 Hz and 2500 Hz should be set to the center frequency.

Power is supplied from the outside to the control unit 2 by means of an electric power unit (not shown).

The transponder 3 mainly includes a coil 3a and a case 3b for housing the coil 3a. The coil 3a is formed by winding a filament-shaped copper wire around a coil former about 88 times. The coil former has a ferrite core. The coil 3a has a reactance of 36 microhenry.

The control unit 2 and the transponder 3 are connected through the coaxial cable 4. The electric signal output from the control unit 2 is sent to the coil 3a of the transponder 3 through the coaxial cable 4.

Figure 3:
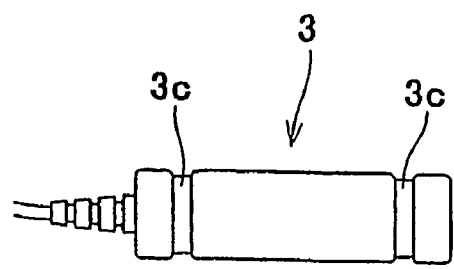
FIG. 3(a) is a side view showing, in detail, a shape of a transponder and the like, FIG. 3(b) is a transverse sectional view showing, in detail, the shape of the transponder and the like, and FIG. 3(c) is a view showing a state in which the transponder is attached to a waterline.
Figure 3:
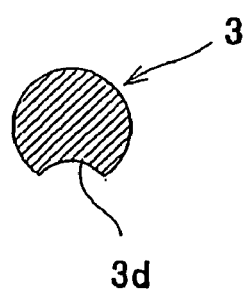
Figure 3:
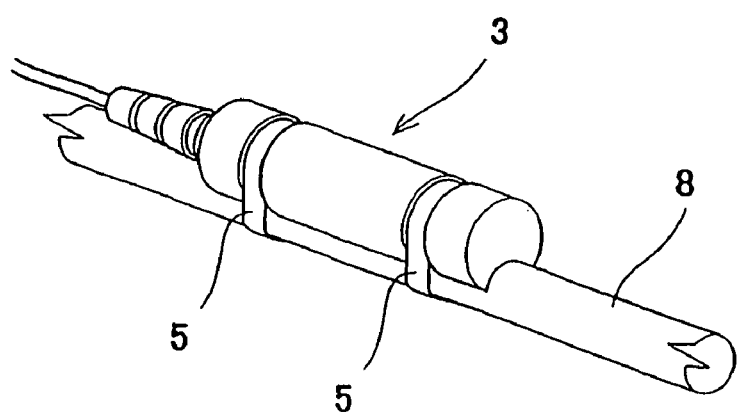

FIG. 3(a) is a side view showing, in detail, a shape of the transponder 3 and the like, FIG. 3(b) is a transverse sectional view showing the same, and FIG. 3(c) is a view showing a state in which the transponder 3 is attached to a waterline.

The transponder 3 has an almost cylindrical shape. A sectional shape of the transponder 3 has a concave portion 3d formed like a circular arc as shown in FIG. 3(b). The concave portion 3d is formed to stabilize the state of attachment to the waterline 8 when the transponder 3 is attached to the waterline 8 of the dental unit 11 and the like (see FIG. 4).

Two trenches 3c are formed on sides of the transponder 3 in a circumferential direction. The trenches 3c are formed in order to fit bind members 5 therein when the transponder 3 is to be attached to the waterline 8 by means of the bind members 5.

Figure 4:
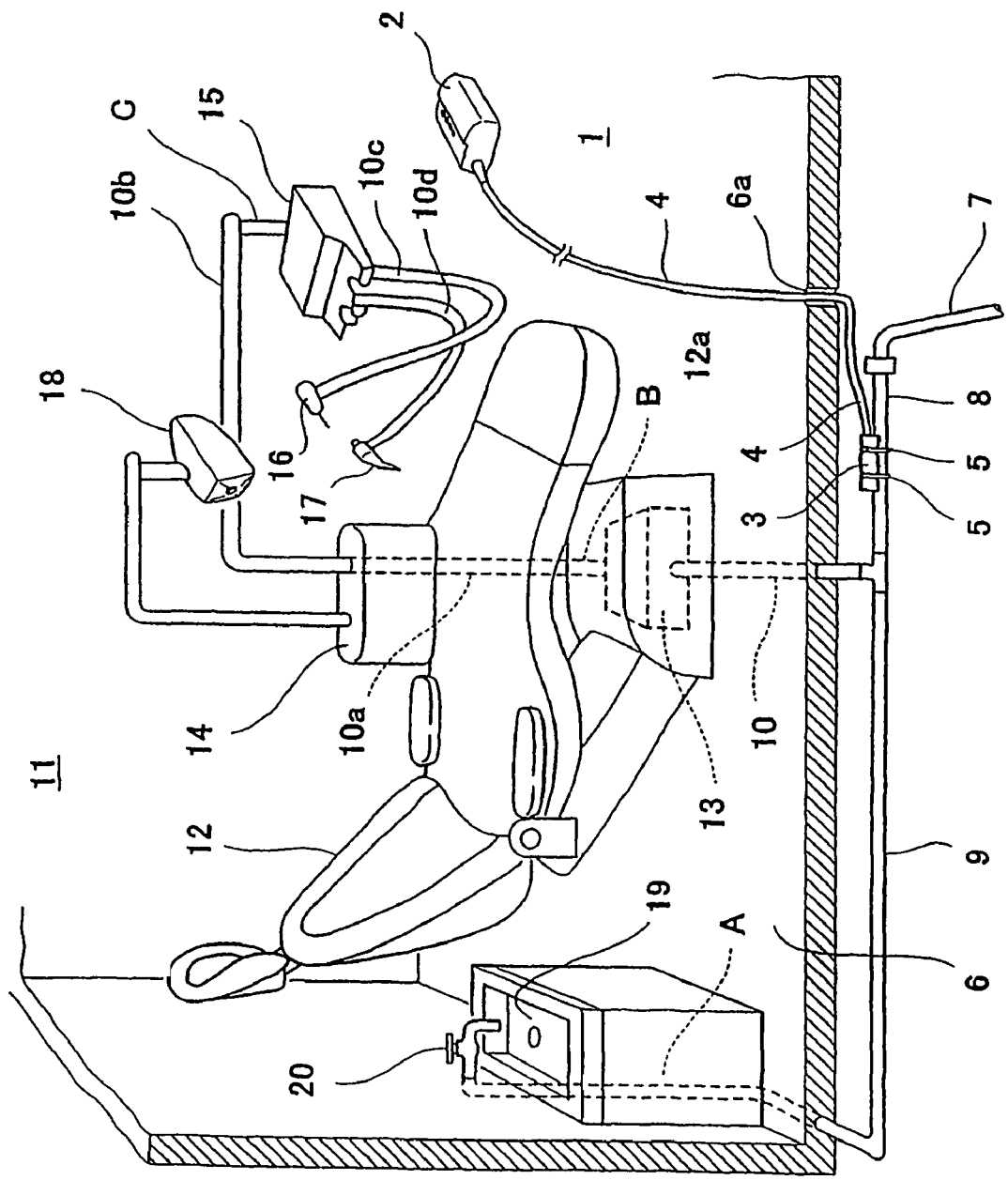
FIG. 4 is a view showing a state of use in which the apparatus according to the present invention is attached to a dental unit.

FIG. 4 is a use state diagram showing a state where the apparatus 1 is attached to the waterline 8 of the dental unit 11.

In FIG. 4, the reference numeral 6 denotes the floor of a room of a dental clinic in a building. On the floor 6, the dental unit 11 and a washstand 19 are mounted, and a main pipe 7 to which service water is supplied is extended under the floor in a hidden state.

The reference numeral 8 denotes a waterline as the transmission source of water connected to the main pipe 7. From the water line 8, a water line 9 and a water line 10 each having a diameter smaller than that of the water line 8 are branched. To the end of the waterline 9, a tap 20 provided for the washstand 19 is connected. To the end of the waterline 10, a connection box 13 is connected. To each of them, service water from the main pipe 7 side is sent.

The reference numeral 11 denotes the dental unit. In a seating 12a of a dental chair 12, the connection box 13 is provided. A unit body 14 is disposed on one side of the dental chair 12.

To the connection box 13, an airline (not shown in FIG. 4) from a compressor for discharging compressed air is connected. To the connection box 13, an electric scaler for removing tartar and a mouth rinse water supplier for supplying water used to rinse the mouth are connected via waterlines each having a small diameter.

To the unit body 14, a waterline 10a and an airline disposed so as to be hidden from the connection box 13 side are connected. An exposed waterline 10b is extended from the unit body 14 and is connected to the control center 15 side. The waterline 10b is connected to the waterline 10a. The reference numeral 18 denotes an illuminating lamp attached to the unit body 14.

To the control center 15, tubular waterlines 10c and 10d are connected. A hand piece 16 for grinding a tooth is attached to the end of the waterline 10c and a syringe 17 for washing the mouth is attached to the end of the waterline 10d.

To the control center 15, a tube (not shown in FIG. 4) to which a vacuum cleaner for discharging water is attached, a foot switch and other operation switches as operation parts, and a lead wire from a relay switch or the like are also connected.

By operating the operation parts (not shown), the control center 15 constructed as described above receives service water from the waterline 10b and high-pressure air from the airline, and sends high-pressure water to the handpiece 16 side via the waterline 10c. It makes the turbine cutter of the head of the handpiece 16 rotate at high speed. By operating the operation parts, low-pressure water is sent to the syringe 17 side via the waterline 10d, so that service water can be supplied into the mouth. In such a manner, treatment of teeth can be performed.

As shown in FIG. 4, the transponder 3 is attached to the waterline 8 connected to the main pipe 7. The reason why the transponder 3 is attached in this position is because service water flows from the main pipe 7 to the dental unit 11 and the washstand 19 side via the waterlines 8, 9, and 10, and an audio electronic signal which will be described later propagates by using, as electric conductor, the service water flowing toward the waterlines 10a to 10d and the like of the dental unit 11.

The transponder 3 is firmly attached to the waterline 8 by allowing a concave portion 3d of the transponder 3 to come in contact with the external wall of the waterline 8 and, after that, binding the transponder 3 and the waterline 8 in a state where the two bind members 5 are fit in the trenches 3c.

The coaxial cable 4 whose one end is connected to the control unit 2 is inserted in a through hole 6a opened in the floor 6, and the other end of the coaxial cable 4 is connected to the transponder 3.

In such a manner, the transponder 3 can be easily attached to the waterline 8 without taking the waterline 8 as the transmission source of water for coupling the main pipe 7 and the waterlines 9 and 10 from the main pipe 7.

As described above, the electric signal is sent from the control unit 2 to the coil 3a in the transponder 3.

Consequently, the transponder 3 generates, in the waterline 8, an audio electronic signal which frequency-modulates in a range of 2000 Hz±40 Hz. Harmonics are also generated on the audio electronic signal by the frequency modulation.

In other words, the audio electronic signal includes a frequency component which fluctuates around 2000 Hz, and a harmonics component. The harmonics can make effects of the present invention (effects of prevention of growth of microbia and removal of the microbia) more remarkable.

Such an audio electronic signal is sent through the waterlines 8,9,10. The transponder 3 is in contact with the waterline 8 in the concave portion 3d. Consequently, the audio electronic signal is easily generated in the waterline 8. Ideally, the audio electronic signal sent through the waterlines 8,9,10 has a voltage level of 200 to 600 millivolts.

The audio electronic signal is sent over a whole length of the waterlines 8,9,10,10a–10d. The waterlines 8–10d and the water acting as a medium filled in the waterlines 8–10d function as conductors for sending the audio electronic signal.

The audio electronic signal breaks off an electrochemical adhesion function of individual cells of the microbia, thereby preventing growth of a biofilm of the microbia. Consequently, the microbia cannot adhere to an internal wall of the waterline 8–10d well. Thus, the cells cannot be increased.

As described above, the problem of the conventional technique that service water retained in a waterline is warmed at room temperature and the number of colonies of microbia and bacteria included in one milliliter of service water sharply increases to several hundreds of thousands toward the end is solved.

Therefore, service water including a small number of colonies can be used for treatment of a patient, so that a cause of diseases can be removed and the problem of infection in a clinic or hospital can be also prevented.

In the above-mentioned embodiment, one transponder 3 is attached to the waterline 8 only. One transponder can prevent the biofilm of the microbia from growing over the whole length of the waterline which is not greater than 30 m. If the waterline has a length greater than 30 m, it is preferable that a plurality of transponders should be attached to the waterline.

In the case where each of the waterlines 8 to 10d is shorter than 30 m, the position of attaching the transponder is preferred to be near the end of the waterline as described above.

Although the transponder 3 is attached to the waterline 8 in the foregoing embodiment, the transponder 3 may be attached to any of the waterlines 8, 9, 10, 10a, 10b, and 10c for the dental unit 11. For example, the transponder 3 may be attached to any of a pipe line A of the waterline 9 to which the tap 20 as the end side of the waterline 8 is connected, a pipe line B of the waterline 10a near the outlet side of the connection box 13, or a pipe line C of the waterline 10b near the inlet side of the control center 15. It is also possible to attach the transponders 3 to the plurality of positions and connect the transponders 3 to the control unit 2 via the coaxial cables 4.

It is also possible to connect a plurality of transponders 3 to one control unit 2 via the coaxial cables 4, and attach the transponders 3 to waterlines of a plurality of dental units 11. With the configuration, in a dental clinic having a plurality of dental units, the apparatus of the present invention can be effectively used.

The present invention is carried out in the above-mentioned form and has the following effects.

(1) According to the apparatus and method of the present invention, growth of microbia in a waterline of a dental unit can be prevented by an audio electronic signal. The audio electronic signal is sent through a waterline so that an effect of prevention of the growth of the microbia can be obtained within a wide range of the waterline connected to the dental unit. Furthermore, a transponder can easily be attached to the waterline.

(2) In particular, if an electric signal frequency-modulates around a predetermined frequency and the frequency modulation causes the audio electronic signal to include a harmonics component, the effect of the prevention of the growth of the microbia can be made remarkable.

(3) If a face of the transponder which comes in contact with the waterline has a concave shape whose section is circular, the transponder can stably be attached to the waterline.

The invention claimed is:

1. An apparatus for preventing growth of microbia propagating themselves on an internal wall of a waterline of a dental unit or for removing the microbia, comprising:
    electric signal generating means for generating an electric signal including an audio frequency component;
    a transponder including a coil and a case for housing the coil; and
    means for attaching the transponder to an external wall of the waterline,
    wherein the electric signal is applied to the coil so that an audio electronic signal to be sent through the waterline can be generated.

2. The apparatus according to claim 1, wherein the electric signal frequency-modulates around a predetermined frequency.

3. The apparatus according to claim 2, wherein the audio electronic signal includes a harmonics component by the frequency modulation.

4. The apparatus according to claim 3, wherein the predetermined frequency is between 1500 Hz and 2500 Hz.

5. The apparatus according to claim 3, wherein a face of the transponder which comes in contact with the waterline has a concave shape whose section is circular.

6. The apparatus according to claim 2, wherein the predetermined frequency is between 1500 Hz and 2500 Hz.

7. The apparatus according to claim 6, wherein a face of the transponder which comes in contact with the waterline has a concave shape whose section is circular.

8. The apparatus according to claim 6, wherein the transponder is attached near an end of the waterline.

9. The apparatus according to claim 2, wherein a face of the transponder which comes in contact with the waterline has a concave shape whose section is circular.

10. The apparatus according to claim 1, wherein a face of the transponder which comes in contact with the waterline has a concave shape whose section is circular.

11. The apparatus according to claim 1, wherein the transponder is attached near an end of the waterline.

12. The apparatus according to claim 2, wherein the transponder is attached near an end of the waterline.

13. A method for preventing growth of microbia propagating themselves on an internal wall of a waterline of a dental unit or for removing the microbia, comprising the steps of:
   generating an electric signal including an audio frequency component;
   attaching a transponder including a coil and a case for housing the coil to an external wall of the waterline; and
   applying the electric signal to the coil, thereby generating an audio electronic signal to be sent through the waterline.

14. The method according to claim 13, wherein the electric signal frequency-modulates around a predetermined frequency.

15. The method according to claim 14, wherein the audio electronic signal includes a harmonics component by the frequency modulation.

16. The method according to claim 14, wherein the predetermined frequency is between 1500 Hz and 2500 Hz.

17. The method according to claim 16, wherein a face of the transponder which comes in contact with the waterline has a concave shape whose section is circular.

18. The method according to claim 16, wherein the transponder is attached near an end of the waterline.

19. The method according to claim 13, wherein a face of the transponder which comes in contact with the waterline has a concave shape whose section is circular.

20. The method according to claim 13, wherein the transponder is attached near an end of the waterline.

* * * * *